US006255518B1

(12) United States Patent
Chambers et al.

(10) Patent No.: US 6,255,518 B1
(45) Date of Patent: Jul. 3, 2001

(54) PREPARATION OF FLUORINATED COMPOUNDS

(75) Inventors: Richard Dickinson Chambers; John Hutchinson, both of Durham (GB)

(73) Assignee: F2 Chemicals, Limited (GB)

( * ) Notice: Subject to any disclaimer, the term of this patent is extended or adjusted under 35 U.S.C. 154(b) by 0 days.

(21) Appl. No.: 09/463,268

(22) PCT Filed: Jul. 9, 1998

(86) PCT No.: PCT/GB98/02012

§ 371 Date: Mar. 20, 2000

§ 102(e) Date: Mar. 20, 2000

(87) PCT Pub. No.: WO99/05080

PCT Pub. Date: Feb. 4, 1999

(30) Foreign Application Priority Data

Jul. 24, 1997 (GB) .................................................. 9715510.5

(51) Int. Cl.$^7$ ....................................................... C07F 9/40
(52) U.S. Cl. .......................... 558/141; 558/161; 558/167; 558/178; 558/203
(58) Field of Search .................................... 558/141, 161, 558/167, 178, 179, 203

(56) References Cited

U.S. PATENT DOCUMENTS

| | | | |
|---|---|---|---|
| 4,478,763 | * 10/1984 | McKenna | 558/141 |
| 4,757,127 | * 7/1988 | Tessier et al. | 558/141 |
| 5,142,085 | * 8/1992 | Barry et al. | 558/167 |
| 5,442,084 | 8/1995 | Lai | 558/141 |

FOREIGN PATENT DOCUMENTS

WO95/14646 6/1995 (WO) .
WO97/00848 1/1997 (WO) .

OTHER PUBLICATIONS

F.A. Davis et al.; Selective, Electrophilic Fluorinations Using N–Fluoro–o–benzenedisulfonimide, *J. Org. Chem.* 60:4730–4737 (1995).

Collins et al.; "Synthesis and Gastrointestinal Pharmacology of the 4–Fluoro Analogue of Enisoprost," *J. Med. Chem.* 30:11 1952–1955 (1987).

Davis et al.; "Selective, Electrophilic Fluorinations Using N–Fluoro–o–benzenedisulfonimide," *J. Org. Chem.* 60:15 4730–4737 (1995).

Liu et al.; "Synthesis and Properties of 12–Fluororetinal and 12–Fluororhodopsin. A Model System for $^{19}$F NMR Studies of Visual Pigments," *J. Am. Chem. Soc.* 103:24 7195–7201 (1981).

Machleidt et al.; "Annalen Der Chemie," Liebigs Ann. Chem. Bd. 674:1–10 (1964).

Thenappan et al.; "Alkylation of (Fluorocarbethoxymethylene)tri–n–butylyphosphorane: A Facile Entry to–Fluoroalkanoates," *J. Org. Chem.* 55:8 2311–2317 (1990).

Thenappan et al.; "Reduction–Olefination of Esters: A New and Efficient Synthesis of –Fluoro , –Unsaturated Esters, " *J. Org. Chem.* 55:15 4639–4642 (1990).

Thenappan et al.; "Acylation of Fluorocarbethoxy–Substituted Ylids: A Simple and General Route to –Fluoro –Keto Esters," *J. Org. Chem.* 56:1 273–277 (1991).

Thenappan et al.; "Preparation of –fluoro—per (poly) fluoroalkyl–substituted enol ethers," *Journal of Fluorine Chemistry* 77:45–50 (1996).

Tsai et al.; "A Novel Intramolecular Horner–Wadsworth–Emmons Reaction: A Simple and General Route to –Fluoro–, –unsaturated Diesters," *J. Org. Chem.* 59:23 7085–7091 (1994).

Tsai et al.; "A One–Pot Synthesis of Unsymmetrical and Symmetrical Tetrasubstituted –Fluoro–, –unsaturated Esters," *Phosporus, Sulfur, and Silicon* 105:205–212 (1995).

* cited by examiner

*Primary Examiner*—Floyd D. Higel
(74) *Attorney, Agent, or Firm*—Myers Bigel Sibley & Sajovec, P.A.

(57) ABSTRACT

A method for the preparation of a fluorinated Phosphonate having the formula $(RO)_2PO\ CFR'R''$ comprises treating a phosphonate of the formula $(RO)_2PO\ CHR'R''$, or a metal salt thereof, with fluorine. R is an alkyl group R' is hydrogen or alkyl and R" is hydrogen, alkyl or another group.

15 Claims, No Drawings

PREPARATION OF FLUORINATED COMPOUNDS

This invention relates to the preparation of fluorinated compounds and, in particular, to the preparation of fluorophosphonates.

Trialkylphosphonoacetates and related phosphonates are valuable intermediates in organic syntheses. The corresponding monofluorinated compounds have the potential to be equally valuable and the chemistry of one of them, $(EtO)_2PO.CHF.COOEt$, has been developed extensively by H. Machleit and R. Westenden (*Lieb. Amr. Chem,* 1964, 674, 1), D. J. Burton et. al. (*J. Org. Chem.,* 1990, 55, 2311; *J. Org. Chem.,* 1990, 55, 4639; *J. Org. Chem.,* 1991, 56, 273, *J. Org. Chem.,* 1994, 59, 7085; *Phosphorus, Sulphur and silicon,* 1995, 105, 205; *J. Fluorine Chem.,* 1996, 77, 45), R. S. H. Lui et. at. (*J. Am Chem. Soc.* 1981, 103, 7195) and P. W. Collins et. al. (*J. Med. Chem.,* 1987, 30, 1952).

Most of the material used in these investigations has been prepared by reaction between a trialkylphosphate and ethyl bromofluoroacetate (Arbutzov Reaction and modifications thereof), but while the Arbutzov reaction itself can be carried out in high yield, the preparation of ethyl bromofluoroacetate is a multi-step synthesis. Further, the bromo compounds required to make other fluorinated phosphonates are not readily available. More recently, the lithium salt derived from triethylphosphonoacetate has been treated with the electrophilic fluorinating agent, N-fluoro-o-benzenedisulphonimide (F. A. Davis, W. Han and C. K. Murphy, *J. Org. Chem.* 1995, 60, 4730) to produce the monofluoro derivative. However, the fluorinating agent is expensive to prepare and is not readily available.

Additionally, the use of electrophilic fluorinating agents such as N-fluoro-1,4-diazabicyclo[2.2.2]octane in the selective fluorination of various methylenephosphonate and methylenephosphorane derivates is discussed in U.S. Pat. No. 5,442,084 but, again, fluorinating agents of this type are generally not readily available.

A more convenient and economical technique for the fluorination of organic compounds is via the use of elemental fluorine. However, reactions of this type can be difficult to control in view of the high reactivity of elemental fluorine, although some applications have been successful. Thus PCT Application No WO97/00848 discloses the preparation of certain fluorinated esters from the corresponding hydrogenated esters by reaction with elemental fluorine, and a similar technique is applied to various 1,3-diketones and 1,3-ketoesters to obtain the corresponding fluorinated derivatives in PCT Application No WO95/14646. Such procedures are, however, rarely satisfactory and generally, lead to unspecific multiple substitution of the starting material, carbon-carbon bond cleavage and oxidation.

Surprisingly in the light of the prior art, the present inventors have now disclosed that fluorinated phosphonates can be prepared by treating a salt derived from the parent phosphonate, or by treating the parent phosphonate in the presence of a base, with elemental fluorinne.

According to the present invention there is provided a method for the preparation of a fluorinated phosphonate having the formula $(RO)_2PO.CFR'.R''$ comprises treating a phosphonate of the formula $(RO)_2PO.CHR'R''$, or a metal salt thereof, with fluorine, where R is an alkyl group, R' is hydrogen or alkyl and R'' is hydrogen, alkyl or another group.

Preferably the metal salt is prepared by treatment of $(RO)_2PO.CHR'R''$ with an alkali metal hydride or an alkali metal alkoxide. Preferably the phosphonate of formula $(RO)_2PO.CHR'R''$ is treated with fluorine in the presence of a base.

It is preferred that the group R has from 1–6 carbon atoms and that in the case where R' is alkyl, it has from 1–6 carbon atoms. Where R'' is a group other than hydrogen, it is preferably $—PO(OR)_2$, $—COOR$, $—COOR$, $—CO.R$ or $—CN$.

Preferably the metal salt has the formula $(RO)_2PO.C^-R'R''.M^+$ where M is lithium, sodium or potassium.

Preferably, the fluorine is diluted with an inert gas such as nitrogen, helium or argon. The concentration of fluorine is preferably in the range 1–50% v/v, more preferably from 2–25% v/v and most preferably from 5–15% v/v.

Preferably, the fluorination is carried out in a solvent which is substantially inert to fluorine, such as acetonitrile or propionitrile.

Preferably, the alkali metal salts are formed in acetonitrile but they may also be formed in a solvent such as diethyl ether, tetrahydrofurane or dimethoxyethane. If solvents such as these are used in the formation of the metal salts, it is necessary for acetonitrile or propionitrile to be added and the ether to be removed by distillation before the fluorination is undertaken.

Where fluorination is carried out by passing a stream of diluted fluorine into a solution of the phosphonate in the presence of a base, the solvent is preferably dry acetonitrile and the base is anhydrous potassium fluoride or anhydrous caesium fluoride.

Preferably, the concentration of phosphonate in the solvent is from 0.1 molar to 10 molar, although higher concentrations may be used.

Preferably, the reaction is carried out at a temperature in the range $-60°$ C. to $+150°$ C., more preferably from $-20°$ C. to $+50°$ C. and most preferably from $-10°$ C. to $+15°$ C.

The following examples serve to illustrate the present invention. Except where indicated otherwise, $^1H$, $^{19}F$ and $^{31}P$ NMR spectra were recorded on a Bruker AC250 spectrometer operating at 250 MHz for hydrogen, 235 MHz for fluorine or 101 MHz for phosphorus. $^{13}C$ NMR spectra were measured on a Varian VXR 400 spectrometer operating at 100 MHz or a Varian Gemini 200 spectrometer operating at 50 MHz. Chemical shifts are recorded in ppm from tetramethyl silane, fluorotrichloromethane and phosphoric acid, and coupling constants are in Hz. Mass spectra were measured on a Fisons Trio 1000 mass spectrometer coupled to a Hewlett Packard 5890 II gas chromatograph fitted with a silicone elastomer coated column (SE 30; 25 m., 0.2 mm. i.d.).

EXAMPLE 1

Fluorination of Triethyl Phosphonoacetate

A glass reaction vessel, fitted with a stirrer was purged with nitrogen and charged with sodium hydride (1.1 gm in oil, i.e. 0.66 gm. 30 mmol. NaH). While maintaining the nitrogen atmosphere, hexane was added to the sodium hydride, the mixture was slurried to wash off the oil, and then the hexane solution was removed with a syringe. Dry acetonitrile was then added to the sodium hydride followed by triethyl phosphonoacetate (4.48 gm, 20 mmol.) which was added dropwise to the stirred slurry. Stirring was continued for one hour before the mixture was cooled to ca. 0° C. and fluorine (50 mmol diluted to 10% v/v with nitrogen) was passed through over a period of 4 hours. After this time, the fluorine was switched off, and the reaction vessel was purged with nitrogen. A weighed amount of trifluoromethyl benzene was then added to the reaction product and from the $^{19}F$ and $^{31}P$ nmr spectra, the amount of recovered starting material and the amount of products formed was calculated. The reaction mixture was poured into water and extracted into dichloromethane. Removal of the solvent gave a mixture of starting material and products which were purified by column chromatography ($SiO_2$/ethyl acetate). The products were i) Triethyl 1-fluorophosphonoacetate (HRMS, Found: $(M+NH_4)^+$ 260.1063. $C_8H_{20}FNO_5P$ requires 260.1063); $\delta_F$-211

(dd,$^2J_{F,P}$ 71.9, $J_{H,F}$ 46.8); $\delta_H$ 1.3 (9H, m), 4.3 (6H, m), 5.2(1H, dd, $J_{H,F}$ 46.8, $J_{H,P}$ 11.7); $\delta_P$ 10.3 (d, $J_{F,P}$ 71.9), $\delta_C$ (100 MHz)13.5 (s, COOCH$_2$CH$_3$), 15.8 (d,$^3J_{C,P}$ 5.7, OCH$_2$CH$_3$), 61.8 (s, COOCH$_2$CH$_3$), 63.7 (t, $^2J_{C,P}$=$^4J_{C,F}$ 6.3, OCH$_2$CH$_3$), 84.4 (dd, $^1J_{C,F}$ 195, $^1J_{C,P}$ 158, CHF), 164.3 (d, $^2J_{C,F}$ 21.7, CO); m/z (CI$^+$, NH$_3$) 260 ((M+NH$_4$)$^+$, 100%), 243 (M+1, 80) and ii) Triethyl 1,1-difluorophosphonoacetate (HRMS, Found: (M+NH$_4$)$^+$278.0969. C$_8$H$_{19}$F$_2$NO$_5$P requires 278.0969); $\delta_F$-117 (d, $^2J_{F,P}$ 96.2); $\delta_H$ 1.4 (9H, m), 4.4 (6H, m); $\delta_P$ 2.96 (t, $J_{F,P}$ 96.2), $\delta_C$ (100 MHz)13.4 (s, COOCH$_2$CH$_3$), 15.9 (d,$^3J_{C,P}$ 5.3, OCH$_2$CH$_3$), 63.4 (s, COOCH$_2$CH$_3$), 65.2 (d, $^2J_{C,P}$ 6.5, OCH$_2$CH$_3$), 110.7 (dt, $^1J_{C,F}$ 271, $^1J_{C,P}$ 203, CF$_2$), 161.4 (q, $^2J_{C,F}$ 18.3, CO); m/z (CI$^+$, NH$_3$) 278 ((M+NH$_4$)$^+$, 100%), 261 (M+1, 20). In this example the conversion was calculated to be 90%, the yield of the monofluorinated phosphonate was 35% and the difluorophosphonate was 15%.

EXAMPLE 2
Fluorination of Triethyl 2-phosphonopropionate

In a similar manner to that described in Example 1, triethyl 2-phosphonopropionate was fluorinated to give triethyl 2-fluoro-2-phosphonopropionate (HRMS, Found: (M+NH$_4$)$^+$274.1220. C$_9$H$_{22}$FNO$_5$P requires 274.1220); $\delta_F$-172 (dq, $^2J_{F,P}$ 83.3, $^3J_{H,F}$ 23.4); $\delta_H$ 1.3 (9H, m), 1.8 (3H, d,d $J_{H,F}$ 23.4, $J_{H,P}$ 15.1), 4.2 (6H, m); $\delta_P$ 13.4 (d, $^2J_{F,P}$ 83.3), $\delta_C$ (100 MHz)13.7 (s, COOCH$_2$CH$_3$), 16.1 (s, OCH$_2$CH$_3$), 19.9 (d, $^2J_{C,F}$ 21.8 CH$_3$CF), 62.1 (s, COOCH$_2$ CH$_3$), 64.0 (dd, $^2J_{C,P}$ 19.1, $^4J_{C,F}$ 6.5 OCH$_2$CH$_3$), 92.7 (dd, $^1J_{C,F}$, $^1J_{C,P}$ 165 and 193. CF), 167.6 (dd, $^2J_{C,F}$ 22.5, $^2J_{C,P}$ 4.9 CO); m/z (CI$^+$, NH$_3$) 274 ((M+NH$_4$)$^+$, 100%), 257 (M+1, 99). The conversion of starting material was 70% and the yield was 35%.

EXAMPLE 3
Fluorination of Tetraisopropyl Methylenediphosphonate

In a similar manner to that described in Example 1, tetraisopropyl methylenediphosphonate was fluorinated to give i) tetraisopropyl fluoromethylenediphosphonate (HRMS, Found: (M+NH$_4$)$^+$ 380.1767. C$_{13}$H$_{33}$FNO$_6$P$_2$ requires 380.1767); $\delta_F$-227 (dt, $J_{H,F}$ 46, $^2J_{F,P}$ 64); $\delta_H$ 1.37 (12H, d, $J_{H,H}$ 6.2), 1.38 (12H, d, $J_{H,H}$ 6.2), 4.8 (5H, m); $\delta_P$ 9.7 (d, $^2J_{F,P}$ 64), $\delta_C$ (100 MHz)23.6 (m, CH$_3$), 24.1 (d, $^3J_{C,P}$ 11.9, CH$_3$), 72.7 (d, $^2J_{C,F}$ 37.8, CH(CH$_3$)), 84.3 (dt, $^1J_{C,F}$ 191.5, $^1J_{C,P}$ 158, CFH); m/z (CI$^+$, NH$_3$) 380 ((M+NH$_4$)$^+$, 24%), 363 (M+1, 100), and ii) tetraisopropyl difluoromethylenediphosphonate (HRMS, Found: (M+NH$_4$)$^+$398.1673. C$_{13}$H$_{32}$F$_2$NO$_6$P$_2$ requires 398.1673); $\delta_F$-123 (t, $^2J_{F,P}$ 87); $\delta_H$ 1.44 (12H, d, $J_{H,H}$ 6.2), 1.46 (12H, d, $J_{H,H}$ 6.2), 4.97 (4H, m); $\delta_P$ 2.3 (t, $^2J_{F,P}$ 87), $\delta_C$ (100 MHz) 23.5 (s, CH$_3$), 24.1 (s, CH$_3$), 74.6 (s, CH(CH$_3$)), 115.5 (tt, $^1J_{C,F}$ 278.8, $^1J_{C,P}$ 189.6, CF$_2$); m/z (CI$^+$, NH$_3$) 398 ((M+NH$_4$)$^+$, 39%), 381 (M+1, 100). The conversion of starting material was 73%, the yield of the monofluoro phosphonate was 50% and the yield of difluoro phosphonate was 10%.

EXAMPLE 4
Fluorination of Dimethyl-2-oxypropyl Phosphonate

A stirred glass reaction vessel charged with dry acetonitrile (50 ml), anhydrous potassium fluoride (5 gm) and dimethyl-2-oxypropyl phosphonate (3.32 gm., 20 mmol) under an atmosphere of dry nitrogen was cooled to ca. 0° C. Fluorine (65 mmol) diluted to 10% v/v was then passed through the mixture over a period of 5 hours. After this treatment, the mixture was filtered and the solids were washed with acetonitrile. The yields and conversion were calculated as in example 1 by adding a weighed amount of trifluoromethyl benzene to the combined filtrate and measuring the $^{19}$F and $^{31}$P nmr spectra. The product, dimethyl-1-fluoro-2-oxypropyl phosphonate (HRMS, Found: (M+NH$_4$)$^+$ 202.0644. C$_5$H$_{14}$FNO$_4$P requires 202.06445); $\delta_F$-208 (d,d,q, $^2J_{F,P}$ 71.3, $^2J_{HF}$ 47.8, $^4J_{HF}$ 4.5); $\delta_H$ 2.39 (3H, d, $^4J_{HF}$ 4.5, CO.CH$_3$), 3.9 (6H, d, d, $^2J_{H,P}$ 10.8, J 2.9, CH$_3$OP), 5.25 (1H, d,d, $^2J_{H,F}$ 47.7, $^2J_{H,P}$ 14.4, CHF); $\delta_P$ 12.7 (d, $^2J_{F,P}$ 71.2), $\delta_C$ (50 MHz) 26.5 (s, CH$_3$O.C), 54.2 (d,d, $^2J_{C,P}$ 6.6, $^4J_{C,F}$ 2.0, CH$_3$OP), 91.0 (d,d, $^1J_{C,F}$ 196.5, $^1J_{C,P}$ 152.5, CHF), 200.5 (d, $^2J_{C,F}$ 20.2, CFHCO); m/z (CI$^+$, NH$_3$) 202 ((M+NH$_4$)$^+$, 10%), 128 (100), was isolated as described in example 1. The conversion was 50% and the yield was 28%.

EXAMPLE 5
Fluorination of Dimethyl-2-oxypropyl Phosphonate

A stirred glass reaction vessel charged with dry acetonitrile (70 ml), sodium ethoxide (1.6 gm., 23 mmol) and dimethyl-2-oxypropyl phosphonate (3.32 gm., 20 mmol) under an atmosphere of dry nitrogen was stirred for 1 hour and room temperature, then cooled to ca. 0° C. Fluorine (65 mmol) diluted to 10% v/v was passed through the mixture over a period of 5 hours. After this treatment the yields and conversion were calculated, as in example 1, by adding a weighed amount of trifluoromethyl benzene to the reaction product and measuring the $^{19}$F and $^{31}$P nmr spectra. The product, dimethyl-1-fluoro-2-oxypropyl phosphonate, was isolated as described in example 1. The conversion was 28% and the yield was 40%.

What is claimed is:

1. The method for the preparation of a fluorinated phosphonate having the formula (RO)$_2$PO.CFR'.R" comprises treating a phosphonate of the formula (RO)$_2$PO.CHR'R", or a metal salt thereof, with fluorine, where R is an alkyl group, R' is hydrogen or alkyl and R1" is hydrogen, alkyl or a —PO(OR)$_2$, —COOR, —CO.R or —CN group.

2. The method according to claim 1 wherein the metal salt is prepared by treatment of, (RO)$_2$PO.CHR'R" with an alkali metal hydride or an alkali metal alkoxide.

3. The method according to claim 1 wherein a phosphonate of formula (RO)$_2$PO.CHR'R" is treated with fluorine in the presence of a base.

4. The method according to claim 1, wherein the group R has from 1–6 carbon atoms and, in the case where R' is alkyl, it has from 1–6 carbon atoms.

5. The method according to claim 1 wherein the metal salt is a salt of lithium, sodium or potassium.

6. The method according to claim 1 wherein the fluorine is diluted with an inert gas.

7. The method according to claim 6 wherein the fluorine is used in a concentration in the range 1–50% v/v.

8. The method according to claim 7 wherein the concentration of fluorine is from 2–25% v/v.

9. The method according to claim 8 wherein the concentration of fluorine is from 5–15% v/v.

10. The method according to claim 1 wherein the fluorination is carried out in a solvent which is substantially inert to fluorine.

11. The method according to claim 10 wherein the solvent is acetonitrile or propionitrile.

12. The method according to claim 1 wherein the reaction is carried out in a solvent and the concentration of phosphonate in the solvent is from 0.1 molar to 10 molar.

13. The method according to claim 1 wherein the reaction is carried out at a temperature in the range −60° C. to plus 150° C.

14. The method according to claim 13 wherein the reaction temperature is from −20° C. to +50° C.

15. The method according to claim 14 wherein the reaction temperature is from −10° C. to +15° C.

* * * * *